United States Patent [19]
Roos et al.

[11] Patent Number: 4,481,466
[45] Date of Patent: Nov. 6, 1984

[54] PULSE AMPLIFYING SYSTEM

[75] Inventors: Ermi Roos, Hialeah; Robert L. Talbert, Pembroke Pines, both of Fla.

[73] Assignee: Coulter Electronics, Inc., Hialeah, Fla.

[21] Appl. No.: 203,122

[22] Filed: Nov. 3, 1980

[51] Int. Cl.³ .............................................. G01N 27/00
[52] U.S. Cl. .................................. 324/71.1; 328/128; 330/107; 377/12
[58] Field of Search ................. 324/71 CP, 71.1, 71.4, 324/77 F, 78 F; 235/92 PC; 330/294, 107; 328/128; 307/490, 520, 521; 377/10, 11, 12

[56] References Cited
U.S. PATENT DOCUMENTS

| | | | |
|---|---|---|---|
| 3,369,186 | 2/1968 | Lejon | 330/294 |
| 3,828,259 | 8/1974 | Riethmuller et al. | 328/128 |
| 3,831,087 | 8/1974 | Schulz et al. | 324/71.1 |

OTHER PUBLICATIONS

"Principles of Electric Instrumentation", 2nd Edition, A. James Diefenderfer, 1979, W. B. Saunders Co., Phila.
Handbook of Modern Solid-State Amplifiers, John D. Lenk, 1974, Prentice-Hall, Inc., pp. 340-341.
Wait, J. V., L. P. Huelsman, G. A. Korn, "Introduction to Operational Amplifier Theory and Applications", McGraw Hill, Inc., 1975, pp. 42-47.

Primary Examiner—Michael J. Lynch
Assistant Examiner—Kevin D. O'Shea
Attorney, Agent, or Firm—Stephen A. Roen; Gerald R. Hibnick

[57] ABSTRACT

An amplifier circuit having an input circuit of resistance and capacitance which is a.c. coupled to a source of pulses, and a feedback circuit of resistance and capacitance. The RC time constants of the input and the feedback circuits are made to be approximately equal at the time of pulse input in order to insure an output pulse flat base line without undershoot or overshoot.

25 Claims, 5 Drawing Figures

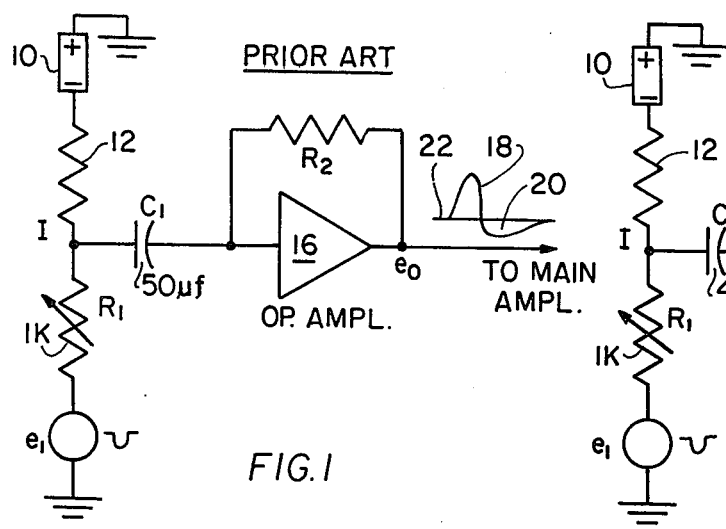
FIG.1 PRIOR ART
FIG.2
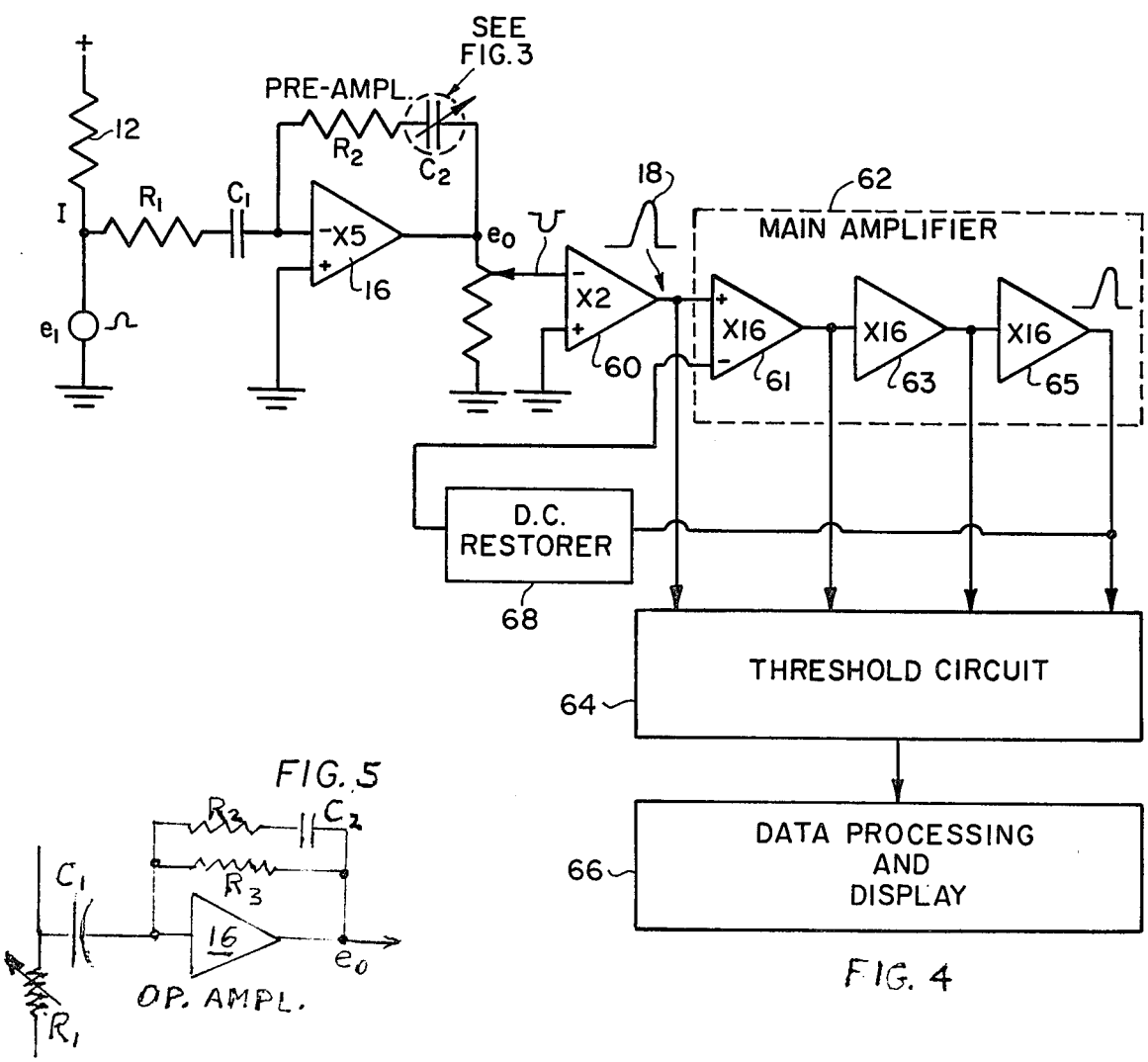
FIG.5
FIG.4

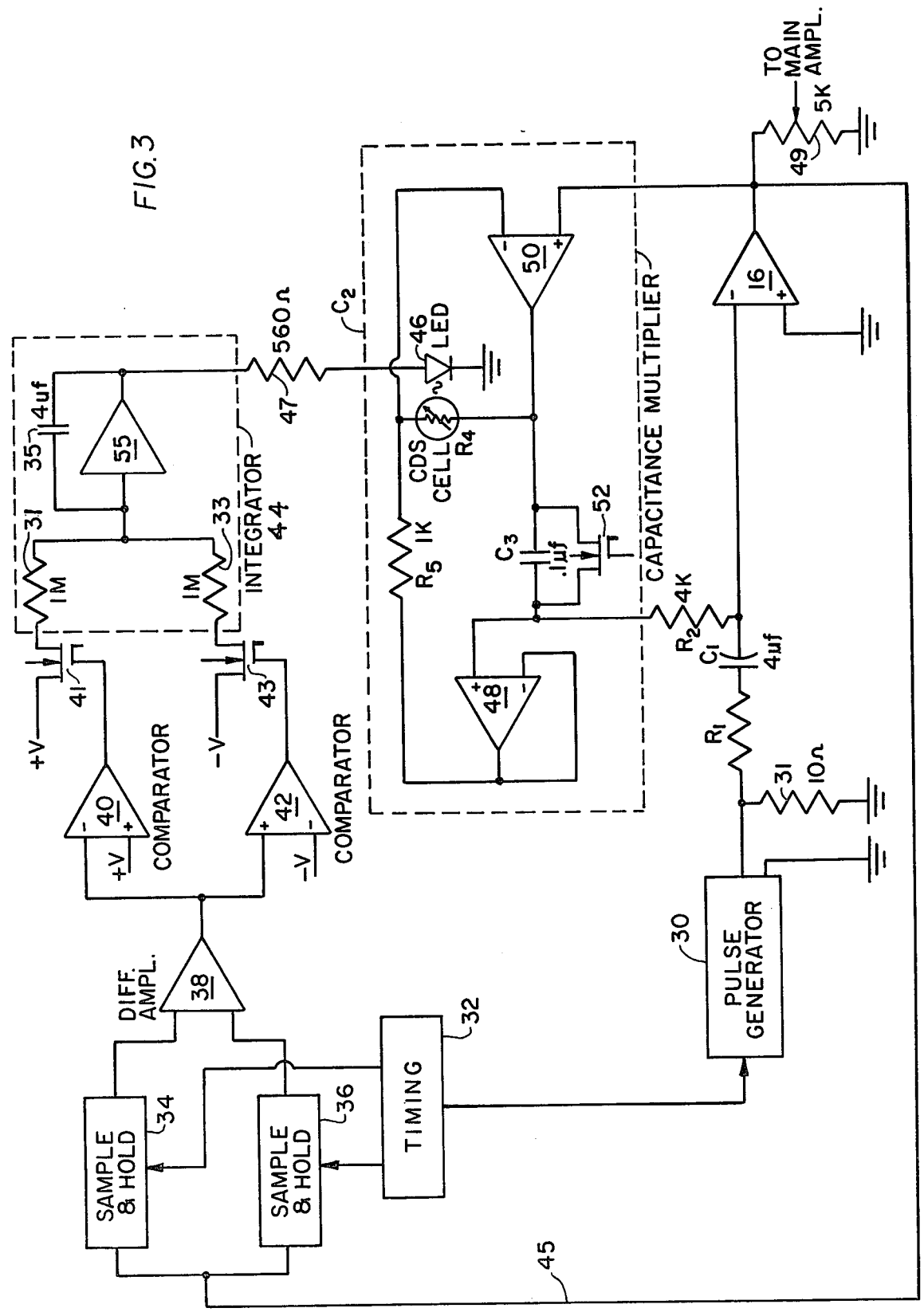

PULSE AMPLIFYING SYSTEM

This invention concerns a method of and apparatus for approximating d.c. coupling in an amplifier which is capacitively coupled to a source of input pulses, such as are produced by microscopic particles passing through an electric sensing zone in apparatus for the analysis of suspended particles.

BACKGROUND

The basic principle of such analysis is referred to as the principle of W. Coulter, which is described in Coulter U.S. Pat. No. 2,656,508. This patent describes an apparatus for counting and classifying microscopic particles suspended in an electrically conducting liquid, such as a saline solution. The electrical conductivity of the liquid is different from that of the particle to be detected and measured. A pair of containers are in fluid communication through a small aperture through which the liquid suspension is caused to flow. The aperture has dimensions which are greater than and are within one to five orders of magnitude of those of the particles. Electrodes are disposed on both sides of the aperture in contact with the liquid and between which a constant current I flows, resulting in a potential difference between these electrodes. The electrical resistance $R_1$ between the electrodes is affected by the presence and size of the particles in the liquid within the aperture. The change $\Delta R_1$ in electrical resistance results in a change of electrical current flowing through the liquid as the particle moves through the aperture. In the Thevenin equivalent of this structure a voltage pulse is generated whose magnitude may be represented by the equation $e_1 = I\Delta R_1$. Thus there are produced a series of discrete signal voltage pulses as the particles move in sequence through the aperture. The amount of resistance change $\Delta R_1$ has been shown to be substantially proportional to both the aperture resistance $R_1$ and the volume of the particle.

Examples of particle analyzing apparatus operating on the principle disclosed in Coulter U.S. Pat. No. 2,656,508 appear in U.S. Pat. Nos. 3,380,584; 3,706,030; 3,710,933; 3,793,587; 3,924,180; and 3,944,917, among others.

Because the voltage across the aperture of an apparatus operating on the principle of W. Coulter normally is very large compared to the signal voltage produced by a particle traversing the aperture, it has been customary to use a.c. coupling between the aperture and the input to the preamplifier of the system. D.C. coupling at this point in the system is undesirable because the high d.c. bias (of the order of 50 volts) sometimes required across the aperture would saturate the amplifier and render it useless. The ratio of signal voltage to the bias voltage may be 1 to 10,000. Where the bias voltage is 50 volts, the signal input voltage may be of the order of 5 mv (Milli-volts).

A.C. coupling to the preamplifier creates problems because of negative undershoot below the base line in the output pulse waveform from the preamplifier. The area of the undershoot equals the area of the pulse above the base line in a.c. coupling. A Coulter Counter ® of the type manufactured by Coulter Electronics, Inc. of Hialeah, Fla., for counting particles is often used to count a wide range of particle sizes within a particle sample, for example, from 2% of aperture diameter to 40% of aperture diameter which represents a particle volume range of 8000:1. Since wide pulse widths are characteristic of large Coulter ® apertures above 500 um (microns) diameter and large time constants are required in the aperture coupling circuit for amplifying wide pulses, the undershoot must become negligibly small before the next succeeding pulse appears in the output of the preamplifier in order to avoid a size error in the measurement of the following particle.

An example of wide pulses is given by a 1,000 um (microns) aperture covering a 1 ms (milli-second) time interval. A narrow pulse may result from a 70 um aperture covering a 20 us time interval. Since the negative undershoot of the preamplifier output pulse caused by capacitive coupling might last for several pulse widths, it is essential to reduce the undershoot to an absolute minimum for longer duration pulses in order to achieve a satisfactory count rate; that is, one that is capable of obtaining a reasonable statistical sample of particles within a reasonable time interval and without appreciable size errors.

If an attempt is made to obtain d.c. coupling by applying a counter or bucking d.c. voltage between the aperture and the preamplifier of a magnitude equal to the aperture voltage, then stability or voltage drift problems are created. Such voltage drift problems are caused by temperature changes in the electrolyte (liquid suspension) and to chemical reactions in the sensor, and would become enormous in the output of the entire amplifier chain due to the high gain needed in the Coulter Counter.

SUMMARY OF THE INVENTION

According to the invention, an a.c. input-coupled operational preamplifier in a particle analyzer is provided with a feedback circuit of a series arrangement of a resistor and a variable capacitance, the multiplied RC values of which establish a clearly specified mathematical relation to the multiplied values of the resistance and capacitance components in the input circuit of the amplifier such that the gain of the amplifier is constant and independent of frequency. The resistance and capacitance components in the input circuit comprise the normal impedance of the aperture in series with a d.c. blocking capacitor which couples this impedance to the input of the preamplifier. The mathematical relationship to be substantially satisfied is $R_1C_1 = R_2C_2$ wherein $R_1$ is the normal resistance of the aperture in the absence of a particle therein, $C_1$ is the d.c. blocking capacitor connecting $R_1$ to the preamplifier, and $R_2$ and $C_2$ are, respectively, the resistance and capacitance in the feedback circuit. The approximate satisfaction of this equation results in an approximated d.c. coupling of the aperture to the input circuit of the preamplifier and the consequent elimination or reduction of undershoot in the output pulses from the preamplifier to an absolute minimum. The presence of a particle within the aperture is only momentary and its presence changes $R_1$ a negligibly small amount in the mathematical relationship of $$R_1C_1 = R_2C_2.$$

An object of the invention is to achieve the effect of d.c. coupling in the input circuit of a preamplifier which is a.c. coupled to the aperture of a particle analyzer operating on the principle of W. Coulter.

Another object is to reduce to a minimum the effect of negative undershoot on a preamplifier, the input of which is capacitively coupled to the aperture of a particle analyzer.

Still another object is to eliminate or reduce to a minimum the deviation of the trailing edge of an output pulse from the base line of the pulse, in an amplifier which has a capacitively coupled input.

A further object is to reduce to a minimum the deviation of the trailing edge of an output pulse from the base line of the pulse appearing in the output of a capacitively input-coupled preamplifier in a particle analyzer which is supplied with input pulses covering a wide range of widths.

A feature of the invention is the feedback circuit for the preamplifier which includes the series arrangement of a fixed resistor and a controlled capacitance multiplier. The capacitance multiplier includes a light emitting diode which is light-coupled to a cadmium sulphide cell. The cell, in turn, is connected across a pair of operational amplifiers. Calibration of the effective overall capacitance is automatically accomplished by sampling the voltage of the base line immediately before and after the application of an input pulse to the preamplifier and comparing the difference. This difference voltage varies the value of the effective overall capacitance. Other objects and features will appear from a reading of the following detailed description.

BRIEF DESCRIPTION OF THE DRAWINGS

FIG. 1 is a schematic diagram of the electrical circuitry of the preamplifier portion of a prior art particle analyzing device. The input of an amplifier is shown capacitively coupled to the aperture which is represented as a variable resistor;

FIG. 2 is a simplified schematic diagram of the electrical circuitry of the preamplifier portion of a particle analyzing device constructed in accordance with the present invention;

FIG. 3 schematically illustrates in more detail the electrical circuitry of the system of the invention in combination with a calibration circuit to accommodate for changes in the feedback capacitor in the preamplifier, in order to establish a clearly specified mathematical relationship;

FIG. 4 schematically illustrates the invention, and shows how, in block form, the preamplifier is coupled to the main amplifier of the particle analyzer and to the threshold and data processing components. This figure is designed to be used with the calibration circuit of FIG. 3 in the manner indicated on the drawing; and FIG. 5 schematically illustrates a portion of the preamplifier part of the particle analyzing device to show how the invention may be utilized without the calibration circuitry of FIG. 3.

Throughout the figures of the drawings the same parts are designated by the same reference numerals.

DESCRIPTION OF THE PREFERRED EMBODIMENTS

The electrical circuit shown in FIG. 1 of the particle-analyzing device operating on the principle of W. Coulter includes a high voltage source 10, a high source resistance 12 (which may or may not be an integral part of the high voltage bias source 10) and a variable load resistance $R_1$ which is the resistance through the aperture in the partition. This load resistance $R_1$ is shown symbolically as a variable resistor in FIG. 1. The electrical signal-detecting circuit includes a high input impedance operational amplifier 16 which has a resistor $R_2$ in its feedback circuit from its output. Resistor $R_2$ sets the gain of the amplifier. The amplifier 16 includes a d.c. blocking capacitor $C_1$ in order to prevent the diversion of aperture current into the input resistance and to prevent the relatively large d.c. component of the voltage across the aperture from saturating the amplifier 16. The operational amplifier 16 is characterized as one having infinite gain for practical purposes. The high voltage source 10 and the high source resistance 12 constitute an essentially constant current supply, such that the current I, which flows through the aperture, is substantially independent of the value of the aperture resistance $R_1$. As a particle passes through the aperture, the resistance changes by an amount $\Delta R_1$ and the essentially constant current flowing through the aperture and the changed resistance of the aperture results in a Thevenin equivalent change of voltage across the aperture which is impressed upon the high input impedance amplifier 16. The signal voltage $e_1$ may be considered to be an a.c. input aperture voltage pulse source equal to $I\Delta R_1$. Voltage $e_1$ results from the passage of a particle through the aperture and may be only a few millivolts or even microvolts compared to the bias voltage of up to 50 volts. The output from the amplifier 16 is indicated by the symbol $e_0$ and represented by the pulse 18. Pulse 18 is shown as having an undesired negative undershoot portion 20 below the base line 22. This undershoot 20 causes the size error problems hereinabove described and which the present invention overcomes.

FIG. 2 shows the invention in simplified form for obtaining an output pulse 18 from the preamplifier 16 which has negligible or no undershoot below the base line 22. Amplifier 16 has a feedback circuit comprising a capacitor $C_2$ in series with a resistance $R_2$. The mathematical relation to be established to achieve the desired result of complete absence of or a negligible amount of undershoot in the trailing edge of the output pulse 18 is given by the equation $$R_1 C_1 = R_2 C_2$$

When this equation is substantially satisfied the amplifier is balanced and an effective d.c. coupling for the preamplifier 16 is obtained, even though the amplifier is coupled to the aperture resistance $R_1$ through a d.c. blocking capacitor $C_1$, and the gain of the amplifier 16 is independent of frequency of the input signal pulses $e_1$. A switch shown herein as a field effect transistor 24 is used for resetting purposes and serves to shortcircuit or discharge variable capacitance $C_2$ between test runs of the samples of the particles (such as biological cells) to be analyzed. Resetting may be done manually.

The foregoing equation $R_1 C_1 = R_2 C_2$ is derived as follows: When the field effect transistor is open (not conducting), the gain of the amplifier 16 is:

$$\frac{e_0}{e_1} = \frac{R_2 + \frac{1}{SC_2}}{R_1 + \frac{1}{SC_1}} = A$$

This is a gain formula given in terms of voltage ratios, and the $(1/SC_1)$ is the impedance of the capacity given in terms of the Laplace Transform. It may also be given as: $(-j/\omega C)$ or $(1/j\omega C)$ As previously noted, $e_1 = I\Delta R_1$ where I is the aperture current and $\Delta R_1$ is the change in resistance of the aperture due to the presence of a particle. The amount of resistance change is assumed to be proportional to both the aperture resistance $R_1$ and the volume of the particle. Hence $\Delta R_1 = KVR_1$, where V is the volume of the particle and K is some constant of proportionality which is characteristic of the aperture. The value of K is determined empircally by putting particles of known volume in the aperture and measuring the change in aperture resistance. Rewriting the foregoing equation:

$$\frac{e_0}{e_1} = \frac{e_0}{KVR_1 I} = \frac{R_2 + \frac{1}{SC_2}}{R_1 + \frac{1}{SC_1}}$$

Since, in the particle analyzer operating on the principle of W. Coulter the amplitude of a pulse is substantially proportional to the volume of a particle, it is desirable to maintain equal pulse amplitude for equal particle volume, regardless of the conductivity of the aperture due to conductivity changes in the electrolyte (for example, a saline solution), such as might be due to a change in temperature and chemical reactions in the electrolyte.

$$\frac{e_o}{V} = \frac{KR_1 I R_2 + \frac{KR_1 I}{SC_2}}{R_1 + \frac{1}{SC_1}} = \frac{F\left(R_1 + \frac{1}{SC_1}\right)}{R_1 + \frac{1}{SC_1}}$$

If the gain is to be independent of frequency, a condition that results in d.c. coupling:

$$F = KIR_2$$

$$\frac{F}{SC_1} = \frac{KR_1 I}{SC_2}$$

$$F = \frac{KR_1 I C_1}{C_2}$$

$$R_2 = R_1 \frac{C_1}{C_2}$$

$$R_2 C_2 = R_1 C_1$$

The foregoing equations indicate that in order for the gain A to be constant, $R_2$ must be constant ($F = KIR_2$). Since the condition of balance is $R_1 C_1 = R_2 C_2$, and $R_2$ must remain constant, and $R_1$ is not controllable, either $C_1$ or $C_2$ must be varied to maintain balance. In the practice of the present invention it is preferred to vary capacitance $C_2$.

Before a particle count or test run can be made, the initial voltage of $C_1$ and $C_2$ must be set. The $C_1$ voltage should be the aperture voltage and the $C_2$ voltage should be zero. These initial conditions are set by the field effect transistor switch 24. When transistor 24 is shorted (conducting), the $C_2$ voltage and the output voltage will be zero, and the junction of $C_1$ and $R_2$ are zero. This junction is zero regardless of the state of transistor 24 because the node voltage is at virtual ground. Capacitor $C_1$ will, therefore, charge to the aperture voltage.

When the transistor 24 is open (non-conducting), the change in charge in the input blocking capacitor $C_1$ is applied to $C_2$ and the ratio of the voltage change between $C_2$ and $C_1$ is equal to the gain A of the amplifier. Therefore, any change in the aperture voltage itself will be coupled through as though it were d.c. coupled. To eliminate voltage drift problems, the preamplifier is reset at the beginning of each run of the particle analyzing apparatus by means of the transistor switch 24 by controls responsive to the push of a button which, in turn, causes the transistor 24 to short (conduct) and then open (cease conducting).

The invention is reset at the beginning of a particle run; hence, initial d.c. conditions are established for each particle run. Because of this resetting aspect, each time a particle run is started the system of the invention becomes relatively insensitive to long term d.c. drift of the aperture voltage. Each reset operation stores the aperture voltage on the input capacitor $C_1$, and removes any voltage from $C_2$. The values given for the components shown in FIG. 2 are for illustrative puposes only.

FIG. 3 diagrammatically illustrates the manner in which the system of the invention can be calibrated before the beginning of each test run by varying the feedback time constant so as to make it equal to the input circuit time constant in order to maintain d.c. coupling. The adjustment in the feedback time constant is done by varying the effective value of capacitance $C_2$ with the aid of a capacitance multiplier. The calibration is done automatically by sampling the voltage of the base line immediately before the leading edge and after the trailing edge of an input pulse, and comparing the difference. This difference voltage varies the effective value of the capacitance in the feedback RC time constant until the difference in the base line voltage is zero.

The calibration system is, in effect, a feedback system which is permanently connected to the preamplifier 16, as shown.

Pulse generator 30 presents a very low impedance (preferably less than 10 ohms which is effectively zero impedance in this context) to the input circuit of the amplifier 16 so that it has negligible effect on the preamplifier when test particle runs are being made. Resistance 31 is a load resistor for the generator 30. During the time test particle sample runs are being made, the oscillator in the generator 30 is turned off. During the calibration process there are no particles in the electrolyte for counting and analyzing. The generator 30 may, for example, generate square wave pulses of one millisecond duration with a 100 cycle per second repetition rate.

A timing control 32 activates the sample and hold circuits 34 and 36 before and after a generator pulse. Sample and hold circuit 34 samples immediately before a generated pulse while sample and hold circuit 36 samples immediately after a generated pulse. Input ramp or base line voltage is applied to the sample and hold circuits from the output of amplifier 16 over a connection 45. The output of timing control 32 provides an interface with the sample and hold circuits and with the pulse generator 30. Control 32 provides shorter square waveform pulses to sample and hold circuits 34 and 36 than to the pulse generator 30, in order to minimize voltage change during the sampling interval. The outputs of the sample and hold circuits are applied to a differential amplifier 38 whose output is connected to two comparators 40 and 42. The comparators constitute threshold detectors which respond to two different voltage levels—one (negative) below and the other (positive) above a predetermined level such as zero volts. When the output of the differential amplifier 38 is high, it causes one comparator, let us say comparator 40, to apply a current of one polarity through its field effect transistor 41 to the integrator 44. When the output of the differential amplifier 38 is low, it causes the other comparator 42 to apply a current of opposite polarity to the integrator 44 through the other field effect transistor 43. Each comparator itself controls the conductivity of its associated field effect transistor.

The integrator 44 includes the 1M resistors 31, 33, the capacitor 35 and an operational amplifier 55. The output of amplifier 55 is a ramp in either the positive or negative direction depending upon which field effect transistor 41 or 43 in the outputs of the comparators is turned on. The output from integrator 44 controls a light emitting diode 46 which, in turn, is light-coupled to a cadmium sulphide photo-conductive cell $R_4$. Resistor 47 is a current limiting resistor for the light emitting diode 46. The light level of LED 46 is a function of current in the output connection from integrator 44. The resistance of cell $R_4$ changes as a function of the integrator voltage until the output of the differential amplifier 38 is between the threshold voltages of the comparators at which time the output of the integrator is constant. The system is calibrated at this point. The adjustment circuitry may be considered to be a negative feedback servo system.

Capacitor $C_3$, cell $R_4$, resistor $R_5$ and operational amplifiers 48 and 50 within the dotted line box $C_2$ form a capacitance multiplier which multiplies the capacitance of $C_3$. Each operational amplifier 48 and 50 have interting (−) and non-inverting (+) input terminals. The ratio of the resistance $R_4$ of the cadmium sulphide cell to the resistance $R_5$ determines the multiplying factor according to the equation:

$$C_2 = \left(\frac{R_4}{R_5} + 1\right) C_3$$

The capacitance multiplier typically can be made to multiply the value of $C_3$ from approximately two to twenty times. Higher multiplication factors are also possible.

The field effect transistor 52 across capacitor $C_3$ is for the purpose of resetting the voltage across $C_3$ immediately before the calibrating cycle begins. This is done automatically by external circuitry not illustrated. Potentiometer 49 is used for calibrating the height of the pulses from the system of FIG. 3.

After the adjustment of capacitance $C_2$ is completed, the particles to be analyzed are placed in the electrolyte (e.g. saline solution) and the test particle run is made.

Typical values for some of the resistors and capacitors shown in FIG. 3, given by way of example only, appear in the drawing.

FIG. 4 diagramatically illustrates the invention coupled to the main amplifier 62 of a particle analyzing apparatus operating on the principle of W. Coulter. The preamplifier 16 has its output coupled to an amplifier 60 which, in turn, is coupled to the main amplifier 62 which comprises a chain of three amplifiers 61, 63 and 65; each providing a gain, by way of example, of sixteen. The capacitance $C_2$ is in the form shown in FIG. 3. The preamplifier 16 may provide a gain of five and the succeeding amplifier 60 a gain of two. The outputs of amplifier 60 and those of the main amplifier 62 are connected to a threshold circuit 64 which may contain analog comparators to analyze particle size. The output of the threshold circuit 64 is connected to a data processing and display system 66. A d.c. restorer 68 in the form of a non-rectifying clamp couples the output of the last amplifier 65 in the chain of amplifiers in the main amplifier 62 to the first amplifier 61 in the chain to generate no undershoot in the output of the last amplifier 65, as contrasted to the use of a rectifying type of clamp. Without the use of d.c. restorer 68 voltage drift at the input of the main amplifier would cause large changes in the voltage of the base line. This clamp 68 may be the kind disclosed in U.S. Pat. No. 3,772,604. This clamp is opened or non-functioning at the occurrence time of the pulse. Since the base line of the pulse 18 is flat at the the input to the main amplifier 62, as shown, when there is no pulse present, there is no amplification of negative undershoot, which would be the case without the present invention.

FIG. 5 illustrates a modification to the invention as shown in FIG. 2. A resistor $R_3$ is connected in parallel across the resistance $R_2$ and the capacitance $C_2$. The resistor $R_3$ has a much higher resistance than resistance $R_2$ provides d.c. stability to the amplifier 16, so as to prevent voltage drift. For example, $R_3$ may be 100K and $R_2$ may be 5K. The resistor $R_3$ also provides a discharge circuit for the capacitance $C_2$; hence, the transistor 24 of FIG. 2 is not necessary with this modification. By virtue of the arrangement, a preselected capacitance value can be used for the capacitance $C_2$ which will approximately satisfy equation $R_1C_1 = R_2C_2$ for a given aperture resistance, i.e., aperture size. As an example, for an aperture diameter size of 2000 microns, capacitance $C_2$ can be 0.8 microfarads. For different aperture resistances, different capacitance values would be required for the capacitance $C_2$.

In comparison to the invention according to FIGS. 1 through 4, the invention according to FIG. 5 does not have automatic adjustment of the capacitance $C_2$ through a servo system. Since the capacitance $C_2$ is not continuously adjusted to correct for drift, such as that caused by temperature variations, the resistor $R_3$ is included for stability. Because of the relatively high resistance of $R_3$, it can be ignored in the calculation of equation $R_1C_1 = R_2C_2$. It should be understood that this equation needs only to be approximately satisfied and that minor variations therefrom are acceptable. The embodiments of FIGS. 2 to 5 allow the use of smaller values for the capacitance $C_1$ than for that for the FIG. 1 circuit of the prior art with a consequent reduction in size in the interest of compactness and a reduction in cost.

An important advantage of the invention, in addition to those which appear hereinabove, is that it greatly reduces the data collection time of certain prior art Coulter type particle analyzers by a factor of up to about 10:1. In these prior art systems, in order to reduce the problems of undershoot the liquid suspension had to be extremely dilute which, of course, greatly reduced the number of particles scanned per unit of time.

The principles of the invention herein described are not limited to the prevention or reduction of the negative undershoot in an a.c. input coupled amplifier. The invention is equally applicable to eliminating or rendering negligible the positive overshoot in a negative output pulse. This negative output pulse can be achieved in a particle analyzer operating on the principle of W. Coulter merely by reversing the direction of the constant current flowing through the aperture or by changing the polarity of the preamplifier output. The invention is also useful in optical type scanners, and its most useful results appear when the dynamic range of the particles is very large, though it does have beneficial results within the narrower dynamic ranges, such as may be encountered in the analysis of blood cells.

What is claimed is:

1. The method of achieving a flat base line in the pulse output of a capacitively input-coupled amplifier which is supplied with a train of input pulses $e_1$, wherein said pulses result from a momentary change $\Delta R_1$ in resistance $R_1$ in a series path of said resistance $R_1$ and a capacitance $C_1$ in the input circuit of said amplifier, which comprises feeding the output $e_0$ of said amplifier back to said input circuit over a series path of a fixed resistance $R_2$ and an effective capacitance $C_2$, and selecting said capacitances such that the gain of the amplifier is independent of frequency and the following equation is satisfied:

$$R_1C_1 = R_2C_2.$$

2. The method of claim 1, wherein the step of selecting said capacitances comprises electronically varying one of said capacitances in such a direction that the gain of the amplifier is substantially independent of frequency and said equation is approximately satisfied.

3. The method of claim 2, wherein $C_2$ is the capacitance which is electronically varied.

4. The method as recited in claim 1, wherein the gain of the amplifier is substantially independent of frequency, and wherein the following equation is approximately satisfied:

$$R_1C_1 = R_2C_2.$$

5. The method of achieving a flat base line in a pulse output of an amplifier in a particle analyzing apparatus wherein particles traverse an aperture having a resistance $R_1$ and through which flows a current I, wherein said amplifier's input is capacitively coupled to said aperture to produce a change $\Delta R_1$ in said resistance $R_1$ to effect voltage pulses representative of $I\Delta R_1$, supplying said pulses through a capacitance $C_1$ to the input of said amplifier, feeding the output of said amplifier back to said input over a series path of resistance $R_2$ and an effective capacitance $C_2$, and selecting said capacitances such that the gain of the amplifier is independent of frequency and the following equation is satisfied:

$$R_1C_1 = R_2C_2.$$

6. The method as recited in claim 5, wherein said capacitance $C_2$ includes a capacitance multiplier.

7. The method of claim 5, wherein the selection of said capacitances is performed manually in a particle analyzing apparatus with a known aperture diameter size so as to satisfy the equation $$R_1C_1 = R_2C_2.$$

8. The method as recited in claim 5 wherein the value of said capacitance $C_2$ is electronically varied in such direction that the gain is independent of frequency and the equation is satisfied.

9. Particle analyzing apparatus having an aperture with an effective resistance $R_1$ through which particles to be measured a capacitor $C_1$ coupling the input of said amplifier to said resistance $R_1$, a series connection of a resistor $R_2$ and an effective capacitance $C_2$ constituting a feedback path between the output and input of said amplifier, the values of $C_1$ and $C_2$ being such as to satisfy the equation:

$$R_1C_1 = R_2C_2.$$

10. Particle Analyzing apparatus in accordance with claim 9, wherein $R_2$ is a fixed resistor.

11. Particle analyzing apparatus as defined in claim 9, wherein said capacitance $C_2$ includes a controlled capacitance multiplier having in its circuit a light emitting diode which is light-coupled to and controls the resistance of a photo-conductive cell, the resitance value of said cell controlling the amount of capacitance multiplication in said multiplier.

12. Particle analyzing apparatus in accordance with claim 9, including a short-circuiting switch connected across said effective capacitance $C_2$.

13. Particle analyzing apparatus according to claim 9, including a field effect transistor coupled across said capacitance $C_2$.

14. In particle analyzing apparatus wherein particles traverse on aperture resistance and through which flows a constant current wherein the variation of aperture resistance through which said constant current flows represents a signal voltage pulse, an amplifier having its input coupled through a d.c. blocking capacitor to said aperture resistance in a series arrangement, a feedback path of fixed resistor and an effective variable capacitor coupled between the output and the input of said amplifier, and means including a negative feedback servo system for varying the value of said variable capacitor in such direction that the gain of said amplifier is independent of the frequency of the input voltage pulses.

15. Particle analyzing apparatus according to claim 14, wherein said means includes an adjustment circuit comprising a pulse generator coupled to the input of said amplifier, a timing circuit for controlling said pulse generator, a first sample and hold circuit controlled by said timing circuit to sample the output of said amplifier immediately before a pulse appears therein, a second sample and hold circuit controlled by said timing circuit to sample the output of said amplifier immediately after a pulse appears therein, whereby the difference in voltage outputs of said sample and hold circuits determines the slope of the base line of the output of said amplifier, a connection from the output of said generator to said first and second sample and hold circuits, a differential amplifier coupled to the outputs of both sample and hold circuits, a first threshold detector comparator operative at a level below zero volts, a second threshold detector comparator operative at a level above zero volts, a common connection from the output of said differential amplifier to both threshold detector comparators, an integrator comprising an operational amplifier connected to the outputs of both comparators, and a circuit coupling the output of said integrator to said variable capacitor, whereby the output of said integrator controls the value of said variable capacitance in such a direction that the slope of the output base line voltage from said first amplifier is decreased to cause a reduction in the voltage difference in the outputs of said sample and hold circuits until the output from said differential amplifier is between the thresholds of said first and second threshold detectors and the output from said integrator is constant.

16. Particle analyzing apparatus in accordance with claim 15, wherein said circuit which couples the output of said integrator to said effective variable capacitor includes a light emitting diode which, in turn, is light-coupled to a photo-conductive cell.

17. Particle analyzing apparatus in accordance with claim 14, including a field effect transistor switch connected across said effective variable capacitor in said feedback path for short-circuiting said capacitance between test runs of the particles to be analyzed.

18. An amplifier having an input circuit a.c. coupled to a source of pulses, and a feedback circuit, both input and feedback circuits having resistor and capacitor components, and means connected to one of said circuits for varying the value of one of said capacitor components so as to maintain equal RC time constants in both said input and feedback circuits, whereby effective d.c. coupling is obtained.

19. An amplifier according to claim 18, wherein said means is connected to the capacitor component in said feedback circuit.

20. An amplifier according to claims 18 or 19, wherein said means includes a capacitance multiplier.

21. An amplifier having an input circuit of a capacitor and a resistance, and a feedback circuit of a capacitor and a resistance, and means coupled to one of said capacitors for varying the value thereof to make the RC time constants of the input and feedback circuits equal, one of said capacitors including a capacitance multiplier comprising first and second operational amplifiers each having an output and inverting and non-inverting input terminals, the series arrangement of a resistor $R_3$ and a photo-conductive cell $R_4$ between the output of said first operational amplifier and the output of the second operational amplifier, a connection from the junction point of said resistor $R_3$ and cell $R_4$ to the inverting terminal of said second operational amplifier, a connection from the non-inverting terminal of said second operational amplifier to the output of said amplifier, a direct connection between the inverting terminal of said first operational amplifier and the output of said first operational amplifier, and a capacitor $C_3$ connected between the non-inverting terminal of the first operational amplifier and the output of said second operational amplifier, the instantaneous value of said feedback capacitor being given by the equation:

$$C_2 = \left( \frac{R_4}{R_3} + 1 \right) C_3$$

and a control circuit comprising a light emitting diode light-coupled to said photo-conductive cell for varying the resistance of said cell as a function of the current flowing through said diode.

22. An amplifier having an effective resistance $R_1$ and a capacitor $C_1$ in series in the input circuit and a resistor $R_2$ and an effective capacitor $C_2$ in series in a feedback path from the output of the amplifier to the input thereof, a resistor $R_3$ having an appreciably higher resistance value than $R_2$ coupled across the series feedback circuit of $R_2$, $C_2$, the values of capacitors $C_1$ and $C_2$ being so chosen as to approximately satisfy the equation $R_1 C_1 = R_2 C_2$ for a predetermined resistance value of $R_1$.

23. Particle analyzing apparatus having an aperture with an effective resistance through which particles to be measured with a constant current I traverse, an amplifier having an input circuit including said effective resistance and said input circuit a.c. coupled thereto, and a feedback circuit, both input and feedback circuits having resistance and capacitance components, and means connected to one of said circuits for varying the value of one of said capacitance components so as to maintain equal RC time constants in both said input and output circuits, whereby effective d.c. coupling is obtained.

24. An amplifier having an input circuit including an effective resistance $R_1$ in series with a capacitor $C_1$ and wherein means varying said resistance $R_1$ produce input signal voltages, comprising:
 a feedback circuit, coupled from the output of said amplifier to its input circuit, including, a resistor $R_2$ in series with an effective capacitance $C_2$;
 a bias voltage source, coupled to said effective resistance $R_1$, for supplying a constant current thereto; and
 means for varying one of said capacitors to approximately satisfy the equation:

$$R_1 C_1 = R_2 C_2.$$

25. An amplifier as defined in claim 24, wherein said resistance $R_1$ is the normal resistance of the aperture of a particle analyzing system in the absence of a particle in said aperture.

* * * * *